(12) United States Patent
Alameh

(10) Patent No.: US 8,179,533 B2
(45) Date of Patent: May 15, 2012

(54) SENSING SYSTEM AND METHOD FOR DISCRIMINATING PLANT MATTER

(75) Inventor: Kamal Alameh, Joondalup (AU)

(73) Assignee: Photonic Detection Systems Pty. Ltd., Subiaco (WA) (AU)

(*) Notice: Subject to any disclaimer, the term of this patent is extended or adjusted under 35 U.S.C. 154(b) by 506 days.

(21) Appl. No.: 12/375,933

(22) PCT Filed: Aug. 1, 2007

(86) PCT No.: PCT/AU2007/001075
§ 371 (c)(1),
(2), (4) Date: Sep. 14, 2009

(87) PCT Pub. No.: WO2008/014553
PCT Pub. Date: Feb. 7, 2008

(65) Prior Publication Data
US 2010/0014096 A1 Jan. 21, 2010

(51) Int. Cl.
*G01N 21/55* (2006.01)
(52) U.S. Cl. .................... 356/445; 356/448
(58) Field of Classification Search .............. 356/445, 356/448
See application file for complete search history.

(56) References Cited

U.S. PATENT DOCUMENTS

| | | |
|---|---|---|
| 3,910,701 A * | 10/1975 | Henderson et al. ............ 356/39 |
| 4,035,070 A | 7/1977 | Hammond |
| 4,911,532 A | 3/1990 | Hidaka |
| 5,132,538 A | 7/1992 | Norris |
| 5,389,781 A | 2/1995 | Beck et al. |
| 5,480,354 A | 1/1996 | Sadjadi |
| 5,507,115 A | 4/1996 | Nelson |
| 5,673,113 A | 9/1997 | Blanc |
| 5,729,473 A | 3/1998 | Blanc et al. |
| 5,789,741 A | 8/1998 | Kinter et al. |
| 6,160,902 A * | 12/2000 | Dickson et al. ............... 382/110 |
| 6,563,976 B1 | 5/2003 | Grann et al. |
| 7,081,611 B2 | 7/2006 | Scott |
| 7,408,145 B2 * | 8/2008 | Holland ....................... 250/221 |
| 7,417,744 B2 * | 8/2008 | Cooke et al. ................. 356/512 |
| 2004/0065834 A1 | 4/2004 | Stone et al. |
| 2005/0098713 A1 | 5/2005 | Holland |
| 2006/0262314 A1 | 11/2006 | Nicolaides et al. |

FOREIGN PATENT DOCUMENTS

| | | |
|---|---|---|
| FR | 2708998 A1 | 2/1995 |
| WO | 9602817 AQ | 2/1996 |
| WO | 9737372 A1 | 10/1997 |
| WO | 9740361 A1 | 10/1997 |

OTHER PUBLICATIONS

Australian Patent Office—International Search Authority (ISA), International Search Report, International Application No. PCT/AU2007/001075, 4 pages, Nov. 13, 2007.

(Continued)

*Primary Examiner* — Roy M Punnoose
(74) *Attorney, Agent, or Firm* — Joshua King; Graybeal Jackson LLP

(57) ABSTRACT

A sensing system comprises a light source having three or more distinct wavelengths for illuminating a plurality of distinct areas in a field of view, a sensor for measuring the reflectance of the distinct areas at each of the distinct wavelengths, and an identifier for identifying at least one object in the field of view from the measured reflectance at each of the wavelengths.

12 Claims, 3 Drawing Sheets

OTHER PUBLICATIONS

Australian Patent Office-13 IPEA, International Preliminary Report on Patentability (IPRP), International Application No. PCT/AU2007/001075, 9 pages, Oct. 31, 2008.

Supplemental European Search Report and European Search Opinion Dated Jul. 7, 2009, for European Patent Application No. EP 07 78 4717 filed Aug. 1, 2007.

* cited by examiner

SENSING SYSTEM AND METHOD FOR DISCRIMINATING PLANT MATTER

PRIORITY CLAIM

The present application is a national phase application filed pursuant to 35 USC §371 of International Patent Application Serial No. PCT/AU2007/001075, filed Aug. 1, 2007, currently pending; which claims the benefit of Australian Patent Application Serial No. 2006904147, filed Aug. 1, 2006, now expired; all of the foregoing applications are incorporated by reference herein in their entireties.

TECHNICAL FIELD

The present invention relates to optical devices and use of optical devices in a sensor for identifying objects.

BACKGROUND

There are a great many needs for sensor systems that can discriminate objects. Such discrimination can be, for example, plant discrimination for horticultural purposes, foreign object detection in industrial processes and in classification systems, to name just a few.

One particular area of interest is in the discrimination of pests in crops. Pests may include insects or weeds. In the area of weed control it is common practice to spray herbicides at different times in the cultivation cycle of a crop. Environmental concerns and increased farm costs have led -to critical evaluation of the use of chemicals in agriculture. Some farming practices have emerged which enable site specific application of chemicals such as herbicide, hence limiting the use of agro-chemicals. The ability to accurately identify and/or differentiate plants in real time and at common operating speeds of farm equipment is regarded as an unmet desire in agriculture.

One vegetation discriminating system known as "the Patchen Weed Seeker" discriminates by measuring the vegetation index (VI) defined as the ratio of reflection at near infrared wavelengths (at around 800 nm) to reflection at red wavelengths (around 650 nm). The VI is high for green plants and low for soil. However this system still has numerous problems including focusing of light from its LED light sources when the target object varies in distance from the LEDs and its ability to discriminate between different green plants with any reliability.

SUMMARY

In a first aspect of the present invention there is a sensing system comprising:

a light source having three or more distinct wavelengths for illuminating a plurality of distinct areas in a field of view;

a sensor for measuring the reflectance of the distinct areas at each of the distinct wavelengths;

an identifier for identifying at least one object in the field of view from the measured reflectance at each of the wavelengths.

In an embodiment the identifier identifies the at least one object by determining a ratio between the measured reflectances at each of the wavelengths.

In an embodiment the light source is configured to sequentially illuminate the distinct areas. In this embodiment the light source produces a narrow beam for sequentially illuminating the distinct areas. In another embodiment the light source is configured to simultaneously illuminate the distinct areas. In this embodiment the light source produces a narrow beam for illuminating each of the distinct areas.

In a second aspect of the present invention there is a sensing system comprising:

a multiple beam light source for producing a plurality of beams of light with each beam having a plurality of distinct wavelengths, the light beams being directed to strike at least one object in a field of view;

a sensor for reading the reflectance of each light beam striking the at least one object.

In an embodiment the beams are parallel to each other.

In an embodiment the light source is configured to sequentially increase the intensity of each light beam.

In an embodiment the sensor is positioned to have a sequentially increased viewing angle of each light beam.

In a preferred embodiment loss due to the sequential increase of the viewing angle is substantially compensated for by the sequential increase in incident beam intensity. In this embodiment the beams of light fall within a common plane, the sensor is located substantially in line with the beams of light and the sensor is located closest to the light beam of weakest intensity.

In an embodiment the light beam at each wavelength is pulsed and the sensor is configured to distinguish the pulses from background light of that wavelength.

In an embodiment the light beam at each wavelength is modulated and the sensor is configured to demodulate the reflected light to distinguish the reflected light from the light source from background light of that wavelength.

In an embodiment the multiple beam light source comprises:

a plurality of lasers, each producing light of different wavelength;

a collimator for collimating the laser beams from the plurality of lasers; and a splitter for splitting the collimated laser beams into a plurality of beams directed at different points in the field of view.

In an embodiment the sensor comprises an intensity detector for each of the light beams. Further, the sensor comprises a lens assembly configured to focus each of the reflected light beams striking the at least one object on to the respective intensity detector. Thus each intensity detector measures the reflected light intensity of the respective incident light beam.

In an embodiment the splitter is configured to produce the light beams parallel to each other.

In a third aspect of the present invention there is a collimated light source comprising:

a first light source which produces collimated light at a first wavelength;

a second light source which produces collimated light at a second wavelength; and a first reflector configured to reflect light at the first wavelength and also configured to pass light at the second wavelength, wherein the first reflector, first light source and the second light source are arranged such that a first light beam from the first source is reflected by the first reflector so as to be collimated with a second light beam from the second light source which passes through the first reflector.

In an embodiment the collimated light source further comprises a third light source which produces collimated light at a third wavelength; and a second reflector configured to reflect collimated light beams at the first and second wavelengths and also configured to pass a collimated light beam at the third wavelength, wherein the third light source, first reflector and second reflector are arranged such that the collimated light beams from the first and second sources are reflected by the second reflector so as to be collimated with a third light beam from the third light source which passes through the second reflector.

In an embodiment the light sources are lasers.

In an embodiment each of the light sources are axially rotatable to change the polarization of the light at the respective wavelength. In a preferred embodiment the axial positions of the light sources are rotated to a position so as to produce the collimated light having the same polarization for all wavelengths.

In a fourth aspect of the present invention there is a collimator comprising:

a first reflector configured to reflect light at a first wavelength and also configured to pass light at a second wavelength; and a second reflector configured to reflect collimated light beams at the first and second wavelengths and also configured to pass a collimated light beam at a third wavelength, wherein the first reflector and second reflector are arranged such that a first light beam at the first wavelength is reflected by the first reflector so as to be collimated with a second light beam at the second wavelength which passes through the first reflector, and the collimated first and second light beams are reflected by the second reflector so as to be collimated with a third light beam at the third wavelength which passes through the second reflector.

In a fifth aspect of the present invention there is an optical device comprising:

an elongate optical cavity having a first end and a second end, a first longitudinal side and a second opposite longitudinal side;

a reflective layer on the first longitudinal side that reflects light inside the optical cavity;

a partially reflective layer on the second longitudinal side such that part of the light in the optical cavity that strikes the partially reflective layer will reflect and part will be transmitted out of the optical cavity; and an optical entry to the cavity in or adjacent to the first end such that light may enter the cavity and be reflected between the longitudinal sides towards the second end, with part of the light exiting the cavity through the second longitudinal side.

In an embodiment the transmissibility of light through the partially reflective layer is substantially constant along its length.

In an embodiment the optical entry is positioned such that the angle of incidence to the normal of the partially reflective layer such that a series of spaced apart parallel light beams are emitted from the optical cavity. Typically the angle of incidence is in the range of 1 to 45 degrees. Preferably the angle of incidence is about 10 to 30 degrees.

In a sixth aspect of the present invention there is an optical device comprising:

a laser;

an elongate optical cavity having a first end and a second end, a first longitudinal side and a second opposite longitudinal side;

a reflective layer on the first longitudinal side that reflects light inside the optical cavity;

a partially reflective layer on the second longitudinal side such that part of the light in the optical cavity that strikes the partially reflective layer will reflect and part will be transmitted out of the optical cavity; and an optical entry to the cavity in or adjacent the first end such that light from the laser enters the cavity and is reflected between the longitudinal sides towards the second end, with part of the light exiting the cavity through the second longitudinal side;

wherein the laser is arranged to emit a light beam through the optical entry at an angle of incidence to the normal of the partially reflective layer such that a series of spaced apart parallel light beams are emitted from the optical cavity.

The spaced apart parallel light beams may be directed at a surface such that they will appear as a line of dots of light.

In a seventh aspect of the present invention there is a method of identification of an object comprising:

providing a database of reference characteristics of candidate objects, each reference characteristic comprising ratios in reflectance intensity of light striking each candidate object at three or more different specified wavelengths;

directing light of at least three of the specified wavelengths at the object;

measuring the reflectance of the light striking the object;

determining the ratio of the measured reflectance;

comparing the determined ratio to the reference characteristics to identify the object.

The object is identified when the determined ratio matches one of the reference characteristics. The candidate object corresponding to the matched reference characteristic specifies the object identified. A match may include a best match or a partial match.

In an eighth aspect of the present invention there is a method of identification of an object comprising:

providing a database of reference characteristics of candidate objects, each reference characteristic comprising ratios of the difference in reflectance intensity of light striking each candidate object at two of three or more different specified wavelengths to the difference in wavelengths between adjacent pairs of the wavelengths;

directing light of at least three of the specified wavelengths at the object;

measuring the reflectance of the light striking the object;

determining the ratio of the difference of measured reflectance to the difference in the wavelengths between each adjacent pair of the specified wavelengths;

comparing the determined ratios to the reference characteristics to identify the object.

In an embodiment the location of the identified object is determined.

In an embodiment the location of the identified object is used to operate a device directed at the identified object. In one embodiment the device is a spraying device.

In an embodiment the candidate objects are plant matter.

In a ninth aspect of the present invention there is a method of discriminating plant matter from other plant matter or other non-plant matter, comprising:

directing a light source having three or more distinct wavelengths at a plurality of distinct areas in a field of view in which the plant matter is contained;

measuring the reflectance of the distinct areas at each of the distinct wavelengths;

identifying the plant matter in the field of view from the measured reflectance at each of the wavelengths at each of the distinct areas.

In a tenth aspect of the present invention there is an apparatus for discriminating plant matter from other plant matter or other non-plant matter, comprising:

a light source arranged to direct light having three or more distinct wavelengths at a plurality of distinct areas in a field of view in which the plant matter is contained;

a sensor for measuring the reflectance of the distinct areas at each of the distinct wavelengths;

an identifier for identifying the plant matter in the field of view from the measured reflectance at each of the wavelengths at each of the distinct areas.

In this specification the term collimated is used to mean a narrow beam with minimal divergence over the useful length of the beam when used in applications suitable for the present invention.

In this specification the term wavelength is used to define a characteristic of light. A person skilled in the art will be readily able to convert the wavelength to frequency of light by use of the well known formula c=λ.f, where c is the speed of light, λ is the wavelength and f is the frequency.

BRIEF DESCRIPTION OF THE DRAWINGS

In order to provide a better understanding of the present invention, preferred embodiments will now be described in greater detail, by way of example only, with reference to the accompanying diagrams, in which.

DETAILED DESCRIPTION

Figure 1:
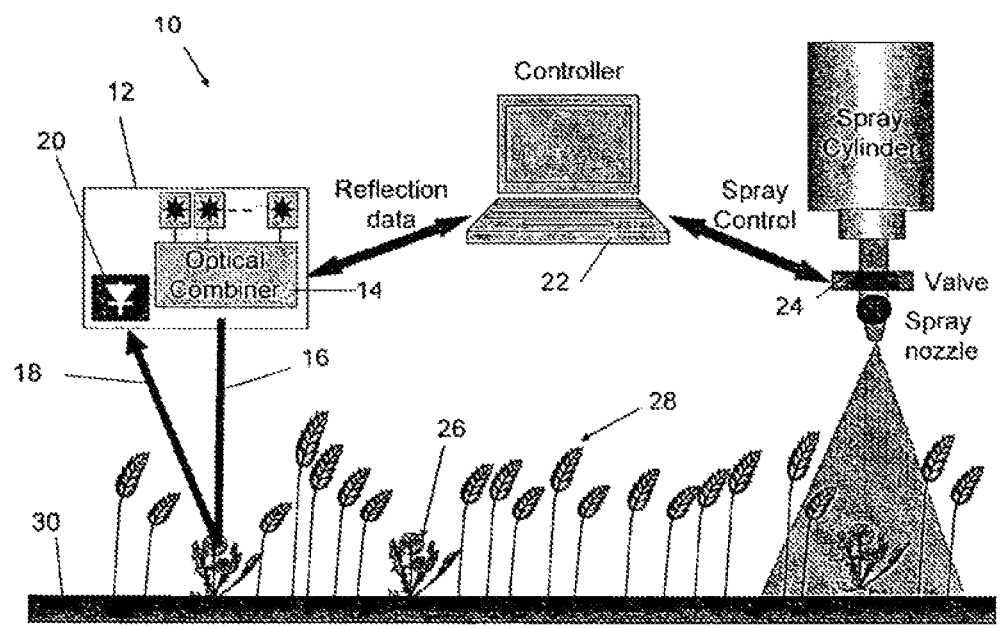
FIG. 1 is a conceptual diagram of a sensing and spraying system according to one embodiment of the present invention.

FIG. 1 shows a sensing and spraying system 10 which comprises a sensing component 12, a controller 22 and a controllable spray unit 24. The system 10 is typically attached to a boom of a piece of farm machinery (such as a tractor) and travels over a crop in a field being cultivated. The direction of travel would be right to left of the diagram. The field has plants 28 of the crop which grow from the ground 30 and unwanted plants, hereafter referred to as weeds 26. The system 10 needs to be able to distinguish not only the ground 30 from the crop 28, but in particular needs to distinguish the weeds 26 from the crop 28. Alternatively the system may be designed to detect other pests such as insects.

The system 10 operates by producing at least one beam of light 16 from a light source 14 of the sensing component 12. The light beam 16 is directed at objects within a field of view as it moves over the field. The transmitted beam 16 is reflected off objects, and in this case a weed 26, to produce a reflected beam 18. A sensor unit 20 of the sensing component 12 detects the reflected beam 18. Measured reflectance data from the sensor unit 20 is sent to the controller 22, which processes the data to identify the object being scanned by the beam 16. The controller 22 is further arranged to control the spray unit 24 so that at the time the spray unit 24 passes over the weed 26, a valve in the spray unit 24 can be operated so as to spray the weed 26 with a suitable chemical, thereby only using the chemical as required. The identification process undertaken by the controller 22 is described below.

In the prior art, the vegetation index is defined as the ratio of reflection at near infrared wavelength (around 800 nm) to the reflection at red wavelengths (around 650 nm). It has been discovered by the inventor that the use of additional wavelengths provides additional ability to discriminate not only plants from soil but also the ability to discriminate between different types of green plant, for which the prior art vegetation index is not reliable.

The present invention achieves this by the light source 14 producing light at three or more different wavelengths. It is desirable to use lasers as the source of light as they are well suited to producing light having very narrow bandwidths. A laser can be regarded as producing light at only the desired wavelength. Each individual laser will produce light at each individual wavelength in an individual beam. In the past complex optics have been used to try to aim light (whether from a laser or not) at a single point having a varying distance from the light source. The inventor has overcome this problem by combining the individual beams into a single combined beam. An embodiment of one aspect of the present invention achieves this by use of a collimator described further below.

Figure 3:
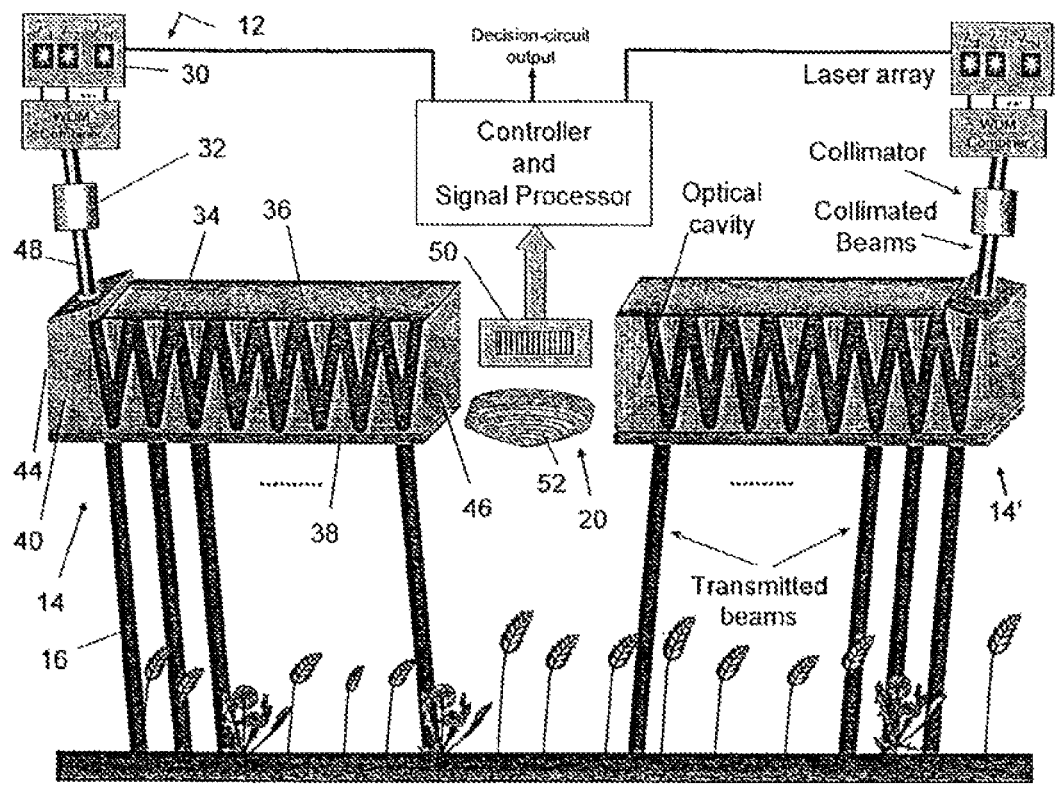
FIG. 3 is a schematic diagram of an embodiment of a sensing system used for weed detection.

Referring to FIG. 3, the sensing component 12 is shown in more detail. The light source 14 comprises a laser array 30, a WDM combiner, a collimator 32, which combines the laser beams from each laser into a single combined beam 48 and a beam splitter 34 which splits the combined beam 48 into a plurality of parallel beams 16 directed at objects in the field of view. An alternative to use of the beam splitter is to scan the beam 16 across a path by moving a reflector so as to direct the beam across the path. The beam 16 may be pulsed so as to illuminate spots as it traverses the path or it may be continuous.

In one embodiment the laser array comprises three AC-driven laser diodes, each producing light at a different wavelength (630 nm, 670 nm and 780 nm). The laser diodes are individually controllable by the controller 22 via a control circuit. The intensity of the beam emitted by each laser can be controlled by a trim-pot.

The WDM beams are overlapped and collimated by the collimator 32. In one embodiment the combined beam 48 has a diameter of 5 mm.

The beam 16 will usually be pulsed/modulated so that upon demodulation the intensity of the reflected beam 18 can distinguished from any background light.

The point of view of FIG. 3 is transverse to the length of travel of the agricultural equipment on which is mounted the system 10 of FIG. 1.

The beam splitter 34 comprises an elongate optical cavity 40, formed of a suitable material, such as glass or clear plastics. The optical cavity 40 could also be formed of a hollow inside of a prism. The cavity 40 has a rectangular prism shape with opposite ends 44 and 46, and parallel, opposite longitudinal sides 36 and 38. It also has an optical inlet 42 into which the combined beam 48 can enter the cavity 40. The inlet 42 is positioned at or near the end 44. A highly reflective coating is applied to the surface of the side 36, which ideally has a reflectance greater than 99%. A partially reflective coating is applied to the second side 38, which reflects approximately 90% of light and transmits approximately 10% of light striking it. This enables the majority of the beam 48 striking the coating to be reflected while allowing some of it to be transmitted. Due to the angle of incidence of the incoming combined beam 48 it reflects between the surface coatings of sides 36 and 38, while at the same time producing a series of parallel beams 16, which are emitted from the side 38. The reflectivity of the coating on the side 38 in this embodiment is constant, but due to the intensity being progressively degraded by each beam transmitted, the internally reflected beam intensity will progressively decrease as it propagates along the length of the cavity 40. This in turn will produce progressively less intense beams 16 further away from the inlet 42 towards the second end 46. The reflectivity/transmissibility of the coating of side 38 need not be constant along the length of the cavity 40 and need not be 90%/10%.

An angle of incidence of the combined beam 48 into the cavity will determined the number of times the beam will be reflected down the length of the cavity 40, which in turn will determine the spacing between each output beam 16.

In one embodiment, the splitter 34 comprises an optical cavity which is a single glass substrate in the shape of a rectangular prism of dimensions 199 mm×29 mm×14 mm, approximately. The ends may be uncoated (clear) so that one can perform as the optical inlet 42.

In this embodiment an angle of incidence of about 19 degrees will produce a beam spacing of about 1 cm. A reasonable practical range of angles of incidence is between 1 and 45 degrees and preferably between 10 and 30 degrees, although any angle between (non inclusive) 0 and 90 degrees may be appropriate depending on the application.

Should it be desired to produce beams 16 that were not parallel then the shape of one or both of the sides 36 and 38 may be varied. For example by making the side 36 concave in shape the beams 16 would diverge, or by making the side 38 concave in shape the beams would converge.

When each beam 16 strikes an object a dot/spot will be illuminated. On a flat surface the beams 16 would form a straight line of dots. The reflection of the illumination, from the point of view of the sensor unit 20, will appear as a reflected beam 18.

The sensor unit 20 is placed substantially in line with the spots, although it may be offset. The sensor unit 20 comprises a one-dimensional imager 50 and an imaging lens 52. The lens 52 focuses each of the points associated with each of the beams onto a sensing element of the imager 50. Thus the elements in the imager are able to produce a one-dimensional image of the reflected beams 18 (i.e. the spots). This one-dimensional image is passed to a precursor signal processor and then onto the controller 22. The precursor signal processor may demodulate the signal and/or correlate the timing of a pulse control signal sent to a particular laser source with the received intensity data in order to match the intensity data with a particular wavelength.

In one embodiment, imager 50 comprises two stacked rows of 1024 pixels, each pixel being 14×14 micrometers in size. The lens 52 has an adjustable iris, zoom and focus to properly capture spots produced by the parallel beams 16 striking objects in the field of view. The lens can have its tilt calibrated in X and Y dimensions so complete spot capture is achieved. The imager 50 is connected to a virtual serial port using a CAT 5 Ethernet cable to a PC (the controller 22) where it is driven using a programmable graphical use interface. Through this interface the sensor's imaging settings can be modified. A series of frames are captured, with each frame including the intensity data. The intensity data of each spot can be measured on a 12-bit intensity scale ranging from 0 to 4096 arbitrary units.

The viewing angle of the sensor unit 20 to each spot will sequentially increase, which in turn will produce a sequential reduction in the perceived intensity in the reflected beam 18. This can be substantially compensated for by the sequential increase in the intensity of the incident beams 16 by placing the sensor unit closest to the light beam 16 of weakest intensity thereby providing it with a viewing angle closest to 0 degrees.

A complementary sensing system 14' can be positioned on the other side of the sensor unit 20. The sensor unit 20 is placed adjacent the end 46 of the splitter 34 so that it is aligned with the line of parallel beam 16. Output of the beams 16 of the system 14 and of the beams from the system 14' can be timed so that the sensor unit 20 can be multiplexed with reflectance readings of the systems 14 and 14'. Indeed the output of each wavelength can be time division multiplexed so that the imager is only reading one wavelength at a time.

Figure 4:
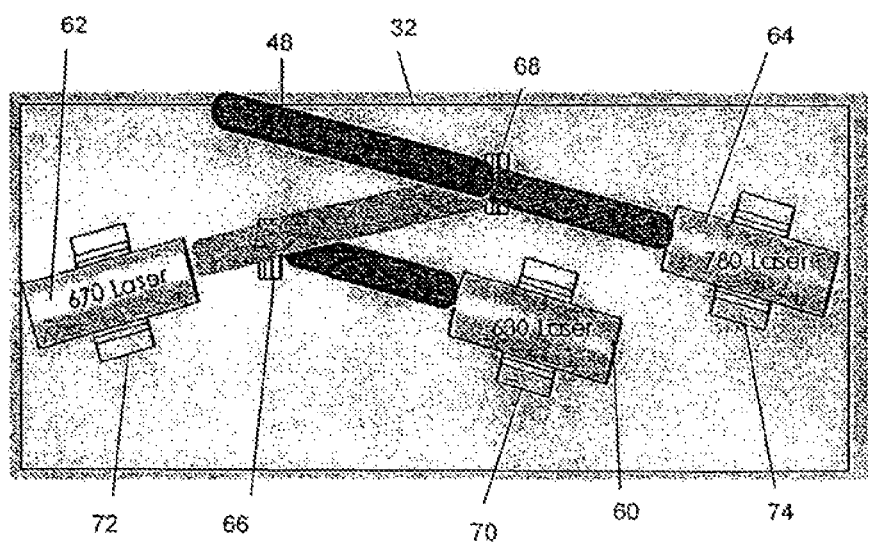
FIG. 4 is a schematic diagram of a source of collimated light in accordance with one aspect of the present invention; and, FIG. 5 is a schematic diagram of a light source according to another embodiment of the present invention.

Referring to FIG. 4, the light source collimator 32 is described in further detail. The laser array 30 comprises first laser 60 producing light of wavelength of about 630 nm, a second laser 62 producing light at 670 nm, and a third laser 64 producing light at a wavelength of 780 nm. The collimator 32 comprises a first reflector 66 and a second reflector 68. Reflectors 66 and 68 comprise thin film optic filters that transmit a particular wavelength incident from one side of the filter and reflect all other wavelengths incident from the other side. In the case of reflector 66 light beam from laser 62 is transmitted whereas the beam from laser 60 is reflected. The lasers 60 and 62 and reflector 66 are aligned so that the reflected beam from laser 60 is aligned and overlaps (is collimated) with the beam from laser 62. The reflector 68 comprises a thin film which allows light from laser 62 to pass therethrough but reflects the combined beam from lasers 60 and 62. The laser 64 and reflector 68 are aligned with reflector 66 such that reflected beams from lasers 60 and 62 are collimated with the beam from laser 64 after it is transmitted through reflector 68. The resultant beam 48 is collimated from the three different lasers.

A person skilled in the art will realize that this technique can be used to add further lasers (potentially of different wavelengths) with use of additional reflectors with appropriate thin film filters. An example of this is schematically shown as collimator 32 in FIG. 5 and described further below. A person skilled in the art will also realize that the collimator will work with only the first laser, the second laser and the first reflector to collimate the beams from the first and second lasers.

Each laser 60, 62 and 64 has a respective mounting 70, 72 and 74 which allow the laser to be rotated about its longitudinal axis. If a polarizing filter is placed in the beam 48 each laser can be rotated so that the beam 48 has the same polarization at each of the wavelengths. For example the first laser 60 is rotated so that light does not pass through the polarizing filter. Then in turn lasers 62 and 64 can be rotated so that again light from those lasers also does not transmit through the polarizing filter. The polarization of each of the lasers will then be the same. It is desirable for the beam 48 to have the same polarization, as different polarization can be a detrimental factor in reading the intensity of the reflected beam 18.

Figure 5:
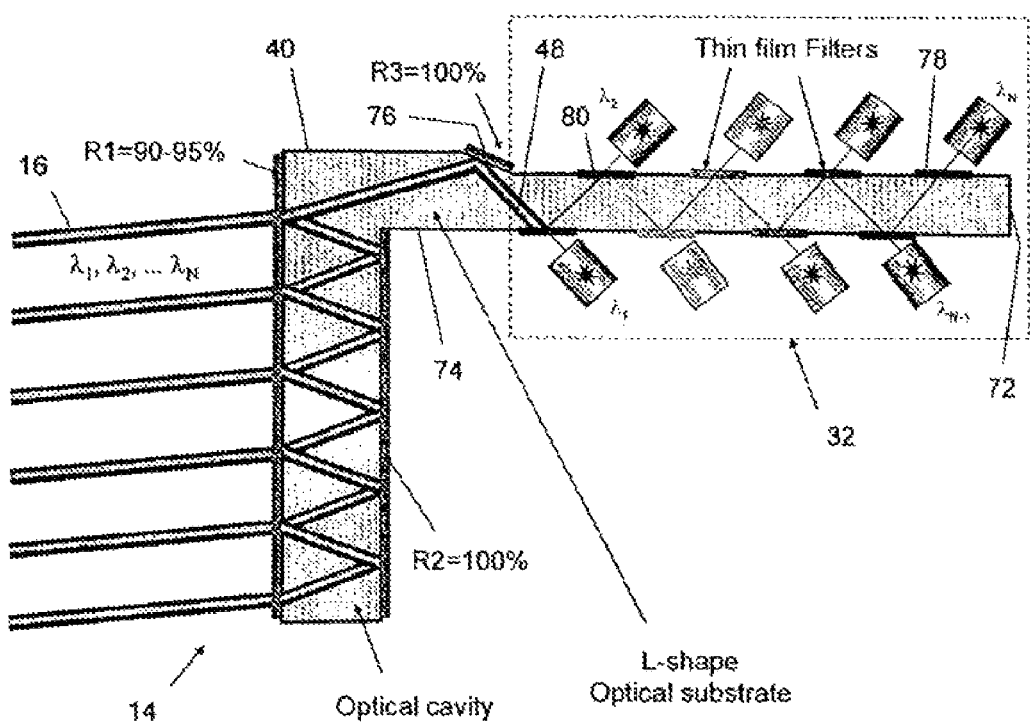

Referring to FIG. 5, an alternative embodiment of the light source 14 is shown. In this embodiment an L-shaped optical substrate formed of glass comprises the optical cavity 40 of the splitter 34 (as the base of the L), a section 72 which comprises a collimator section 72, and section 74, which connects the collimator section 72 to the optical cavity 40. Sections 72 and 74 form the back of the L. The collimator section 72 is formed in a similar arrangement to that shown in FIG. 4 with a plurality of laser sources each producing a different wavelength $\lambda_1, \lambda_2 \ldots \lambda_{N-1}, \lambda_N$ of light and a series of filters 80 situated on the outside of the substrate section 72 which transmits light from the respective laser but reflects light at other wavelengths (e.g., the filter marked 80 transmits light at $\lambda_2$, but reflects other wavelengths). Filter 78 transmits light at wavelength $\lambda_N$. The lasers and filters 78 and 80 are arranged with respect to the section 72 such that the resultant laser beam 48 is collimated. The collimated beam 48 strikes a reflector 76, which has approximately 100% reflection. Reflector 76 is oriented to send the beam 48 into the optical cavity 82 at an angle suitable to produce the desired number of combined output parallel beams 16 due to its reflected propagation from side to side down the length of the splitter 34.

The method of use and operation of the present invention will now be described with reference to the accompanying diagrams.

System 10 is mounted for operation such that objects to be identified travel though the beams 16. In the weed control application the system 10 will be mounted on a boom of an agricultural vehicle, which can travel over the crop at a height of about 1 to 2 m. The system 10 of FIG. 3 can cover 1 to 3 m along the length of the boom and if need be other systems 10 can be placed in parallel on the boom to complete the entire width of the boom. In other applications the system 10 may be stationary and the objects being identified will move by, such as on a conveyor belt.

The light beams 16 strike one or more objects producing a series of illuminated spots. The light may be visible or may be outside the visible spectrum. In the weed control application the 630 nm laser light is visible as red. The 670 nm and 780 nm laser light are in the (near) infrared spectrum and are not visible to the human eye. Other wavelengths may be used in other applications. In the weed control application more wavelengths will produce greater accuracy in discrimination, up to about 10 to 15 different wavelengths.

The reflected light 18 is captured by the sensor unit 20 and a reading of the intensity of each spot is taken. The readings are provided to the controller 22. The controller 22 runs a computer program that normalizes the readings, stores the readings and calculates a ratio between each of the normalized intensities. The normalized intensity ratios are compared to a database of intensity ratios to find a match or best match. In the event a match is found an object classification associated with the matching ratios is used to identify the object.

Due to the linear nature of the spots, the location and even a dimension of the identified object can be determined. This may be combined with GPS information on the location of the vehicle for recording and later analysis. Based on the determined location in the line of dots (and thus the location relative to the boom), the distance between the sensing component 12 and controllable spray unit 24, and the speed of travel of the vehicle, operation of the spray unit 24 can be timed to only dispense the chemical on to the object when it is identified as a weed 26. Usually a line of spray units 24 will be positioned on the boom (or a second trailing boom). By knowing the position of the weed in the line of spots the appropriate spray unit is activated. In the event that the system was configured to detect insects, when an insect is detected it could be sprayed with an insecticide. Likewise in other applications once the object is identified by its ratios of spectral response appropriate action (if any) can be taken.

The database of ratios is constructed by taking sample readings from possible candidate objects. The ratios of intensity of keys wavelengths are recorded in the database along with a classification of the candidate objects for matching against. For example the green leaf in FIG. 2 has a set of ratios of (about) 10.2:10:60.

Figure 2:
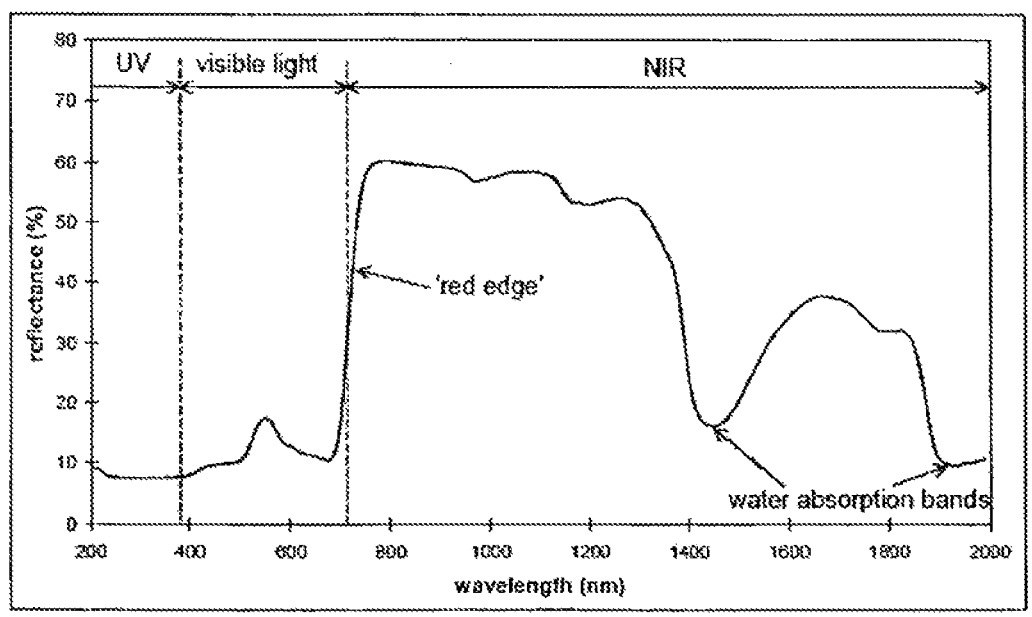
FIG. 2 is a graph showing a typical reflective spectrum (by wavelength) of a green leaf.

An alternative to using ratios of intensities is to use the gradient between adjacent wavelength intensity pairs. The ratios can in fact be used to derive the gradients and vice versa. Again an example of gradients of the green leaf in FIG. 2 are $(10-10.2) \div 40 = -x\ 0.005$ and $(60-10) \div 110 = 0.455$.

Use of the ratios or gradients provides considerably better matching results for identifying objects in the database than the prior method of using a VI because a larger portion of the reflectance spectrum is able to be used in making the match.

The collimator 32 of the present invention can be used in other applications. It operates by receiving light from laser 60 (or some other source of collimated light) and reflecting it off of reflector 66. At the same time it receives light from laser 62 (or another collimated light source). The light from laser 62 is transmitted though the reflector 66 and aligns with the reflected light from laser 60. The light from laser 60 and laser 62 is then collimated. This collimated light can then be reflected off reflector 68. At the same time the collimator 32 receives light from laser 64 (or another collimated light source). The light from laser 64 is transmitted though the reflector 68 and aligns with the reflected light from laser 60 and laser 62. The resulting output beam 48 is an alignment (collimation) of light from lasers 60, 62 and 64. It is readily apparent that further laser of different wavelengths can be added with appropriate reflectors.

The splitter 40 of the present invention can be used in other applications. It operates by receiving light 48 through the optical inlet 42. The light refracts according to the angle of incidence and is partly transmitted through the coating of side 38 to form a first beam 16. It is also reflected by the coating of side 38 and strikes the coating of side 36 further along the length of the cavity towards end 46, whereupon it is again reflected to again strike the coating of side 38. This light is partly transmitted through the coating on side 38 to form a second beam parallel to the first beam. It is also reflected by the coating of side 38 to again strike the coating of side 36 further along the length of the cavity towards end 46. This process continues with the beam bouncing back and forth between sides 36 and 38 down the length of the cavity towards end 46 and produces further beams from side 38 which are parallel to the first and second beams. It is readily apparent that the dimensions of the cavity and the angle of incidence of the input beam will affect the spacing and number of output beams. It is readily apparent that the percentage of transmission/reflectance of the beam through the coating of side 38 will affect the intensity of the output beams.

It will be understood to persons skilled in the art of the invention that many modifications may be made without departing from the spirit and scope of the invention.

The invention claimed is:

1. A sensing system for discriminating plant matter comprising:
   a light source comprising three or more lasers, each producing a laser beam of a different wavelength;
   a collimator for collimating the laser beams from the plurality of lasers into a combined beam;
   a splitter for splitting the combined beam into a plurality of beams each with the three or more wavelengths such that the beams are directed at distinct non-overlapping areas in a field of view:
   a sensor for distinctly measuring the reflectance from each of the distinct non-overlapping areas at each of the distinct wavelengths; and
   an identifier for identifying at least one plant type in the field of view from the measured reflectance at each of the wavelengths at each of the distinct non-overlapping areas.

2. A sensing system as claimed in claim 1, wherein the identifier identifies the at least one plant type by determining a ratio between the measured reflectances at each of the wavelengths and comparing the determined ratio with a database of reference wavelength ratios of known plant matter so as to identify observed plant matter at each of the distinct non-overlapping areas.

3. A sensing system as claimed in claim 2, wherein the identifier comprises:
   a storage for a database of reference characteristics of plant matter of or derived from reflectance intensity of light striking each candidate plant matter at three or more different specified wavelengths; and a processor for determining the ratio of the measured reflectances at each of the distinct non-overlapping areas and comparing the determined ratio to the reference characteristics in the database to identify the plant type.

4. A sensing system as claimed in claim 1, wherein the identifier identifies the at least one plant type by determining gradients between the measured reflectances at each of the wavelengths and comparing the determined gradients with a database of reference wavelength gradients of known plant matter so as to identify observed plant matter at each of the distinct non-overlapping areas.

5. A sensing system as claimed in claim 4, wherein the identifier comprises:
   storage for a database of reference characteristics of plant matter of or derived from reflectance intensity of light striking each candidate plant matter at three or more different specified wavelengths; and
   a processor for determining the gradient of the measured reflectances at each of the distinct non-overlapping areas and comparing the determined gradient to the reference characteristics in the database to identify the plant type.

6. A sensing system as claimed in claim 1, wherein the splitter is configured such that the intensity of each laser beam progressively decreases and the sensor is positioned such that the most intense beam is furthest from the sensor.

7. A sensing system as claimed in claim 1 wherein the collimator comprises:
   a first reflector configured to reflect light at a first of the wavelengths and also configured to pass light at a second of the wavelengths, wherein the first reflector, a first one of the lasers and a second one of the lasers are arranged such that a first laser beam from the first laser is reflected by the first reflector so as to be combined and collimated with a second laser beam from the second laser which passes through the first reflector;
   a second reflector configured to reflect collimated laser beams at the first and second wavelengths and also configured to pass a laser beam at a third of the wavelengths, wherein a third one of the lasers, the first reflector and second reflector are arranged such that the combined laser beams from the first and second lasers are reflected by the second reflector so as to be combined and collimated with a third laser beam from the third laser which passes through the second reflector.

8. A sensing system as claimed in claim 1, wherein the splitter comprises:
   an elongate optical cavity having a first end and a second end, a first longitudinal side and a second opposite longitudinal side;
   a reflective layer on the first longitudinal side that reflects light inside the optical cavity
   a partially reflective layer on the second longitudinal side such that part of the combined laser beams of three or more distinct wavelengths in the optical cavity that strike the partially reflective layer will reflect and part will be transmitted out of the optical cavity; and
   an optical entry to the cavity or adjacent to the first end such that the laser beams may enter the cavity and be reflected between the longitudinal sides towards the second end, with part of the combined laser beams of three or more distinct wavelengths exiting the cavity through the second longitudinal side such that the combined and collimated laser beams are transformed into a plurality of spaced apart laser beams having three or more distinct wavelengths emanating from the second longitudinal side so as to illuminate the plurality of distinct non-overlapping areas in the field of view.

9. A sensing system as claimed in claim 1, wherein the axis orientation of each of the lasers is such that the polarization of the combined laser beams from the collimator is aligned at the three or more wavelengths.

10. A method of identification of plant matter comprising:
    producing a plurality of laser beams each of a different wavelength;
    collimating the laser beams into a combined beam of three or more different wavelengths;
    splitting the combined beam into a plurality of spaced apart beams each with the three or more wavelengths such that the beams are directed at distinct non-overlapping areas in a field of view;
    measuring the reflectance at each of the distinct wavelengths at each of the distinct non-overlapping areas; and
    identifying at least one plant type in the field of view from the measured reflectance at each of the wavelengths at each of the distinct non-overlapping areas.

11. A method as claimed in claim 10, wherein identification of plant matter comprises:
    providing a database of reference characteristics of candidate plant matter, each reference characteristic comprising ratios of reflectance intensities of light striking each candidate plant matter at three or more different specified wavelengths;
    determining a ratio of reflectance intensities of the measured reflectances at three or more different specified wavelengths; and
    comparing the determined ratios to the reference characteristics to identify the plant matter.

12. A method as claimed in claim 10, wherein identification of plant matter comprises:
    providing a database of reference characteristics of candidate plant matter, each reference characteristic comprising gradients between different reflectance intensities of light striking each candidate plant matter at three or more different specified wavelengths;
    determining gradients between different reflectance intensities of the measured reflectances at three or more different specified wavelengths: and
    comparing the determined gradients to the reference characteristics to identify the plant matter.

* * * * *